(12) United States Patent
Gidekel

(10) Patent No.: US 10,194,666 B2
(45) Date of Patent: Feb. 5, 2019

(54) PROCESS FOR REPAIRING DAMAGE TO WOOD AND RELATED CELLULOSIC PRODUCTS CAUSED BY TERMITES AND OTHER WOOD DAMAGING INSECTS

(71) Applicant: Manuel Gidekel, Santiago (CL)

(72) Inventor: Manuel Gidekel, Santiago (CL)

(73) Assignee: ICyT SpA (CL)

( * ) Notice: Subject to any disclaimer, the term of this patent is extended or adjusted under 35 U.S.C. 154(b) by 246 days.

(21) Appl. No.: 15/288,703

(22) Filed: Oct. 7, 2016

(65) Prior Publication Data

US 2017/0332644 A1 Nov. 23, 2017

Related U.S. Application Data

(63) Continuation-in-part of application No. 14/120,777, filed on Jun. 26, 2014, now Pat. No. 9,491,950.

(51) Int. Cl.
| | |
|---|---|
| *A61K 36/00* | (2006.01) |
| *A01N 63/02* | (2006.01) |
| *A01N 25/00* | (2006.01) |
| *A01N 41/06* | (2006.01) |
| *A01N 47/34* | (2006.01) |
| *C12N 1/20* | (2006.01) |
| *B27K 3/00* | (2006.01) |

(52) U.S. Cl.
CPC ........... *A01N 63/02* (2013.01); *A01N 25/006* (2013.01); *A01N 41/06* (2013.01); *A01N 47/34* (2013.01); *B27K 3/002* (2013.01); *C12N 1/20* (2013.01); *B27K 3/00* (2013.01)

(58) Field of Classification Search
CPC ....................................................... A61K 36/00
USPC ......................................................... 424/725
See application file for complete search history.

(56) References Cited

U.S. PATENT DOCUMENTS 8,871,016 B2 * 10/2014 Trexler .................. C08B 1/003
106/164.01

\* cited by examiner

*Primary Examiner* — Michael V Meller
(74) *Attorney, Agent, or Firm* — John Dodds

(57) ABSTRACT

The present invention provides for a process for repairing damage to wood and related cellulosic products caused by termites and other wood damaging insects comprising the steps of providing a modification of the bacteria of the genus *gluconacetobacter* toxic to termites and other wood damaging insects; converting said bacterial modification into a bait attractive to termites and other wood damaging insects as a source of food; and allowing said bacterial modification to produce a by-product ooze capable of repairing would damaged by termites and other wood damaging insects. The process causes the build-up of wood like material, thus effectively repairing the termite damaged areas.

2 Claims, 17 Drawing Sheets

Specification includes a Sequence Listing.

>Gluconacetobacter malus
GTGTAGTTAAGTTTTTACAATACAAGTCGCACGATCTTTTCGGGTTTAGTGGCGGACGGGT
GAGTAACGCGTAGGGATTTATCCACGGGTGGGGAATAATTTTGGAAAACTGAAGCTAATCC
CGCATGACACCTGAGGGTCAAAGGCGCAAGTCCCTGTGGAGAAACCTGCTTTCAATTACC
TAGTTGGGGGGGTAAAGGCCTACCAAGGCAATGATCAATAGCTGGTCTGAGAGGATGATCA
CCCACACTGGGACTGAAACACGGCCCAAACTCCTACGGGAGGCAGCAGTGGGAAATATTGA
ACAATGGGCGCAACCCTGATCCACCAATGCCGCGTGTGTGAAAAAGGTTTTCGGATTGTAA
AGCATTTTCAGCGGGGACAATGATGACGGTCCCCGCAAAAAACCCCCGGCTAATTTCGTG
CCAGCACCCGCGGTAATACAAAGGGGGCAAGCGTTGCTCGAAATGACTGGGCGTAAAGGGC
GCGTAGGCGGTTGACACAGTCAAATGTAAAATTCCCGGGTTTAACCTGGGGGCTGCTTTTG
ATACGTGGCAACTAAAGTGTGAAAAAGGGTTGTGAAATTCCCAGTGTAGAGGTGAAATTCG
TAAATATTGGAAAAAACACCGGGGGCAAAGGCGGCAACCTGGCTCATGACTGACCCTGAGG
CGCAAAAGCGTGGGGAGCAAACAGGATTAAATACCCTGGTAGTCCACGCTGTAAACAATGT
GTGCTGAATGTTGGGTGACTTTGTCATTCAGTGTCGTATTTAACGCGATAAGCACACCGCC
TGGGGAGTACGGCCGCAAGGTTAAAACTCAAAGAAATTGACGGGGGCCCGCACAAGCGGGG
GAGCATGTGGTTTATTTCAAAGCAACGCGCAAAACCTTACCAGGGCTTGACATTGGGAAGG
CCGTGTCCAGAAATGGGCATTTTCTCGCAAAAAAACCTCAACCAACAGGTGCCTGCATGGT
TGTCTCCCTCTCCGGTCCGGGAA

Fig. 1

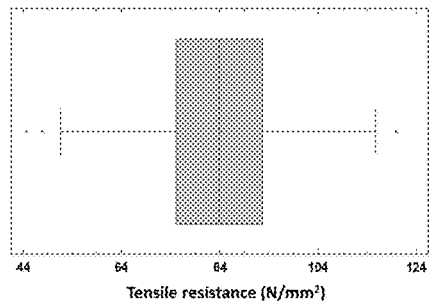
Tensile strength: Box-Cox Diagram
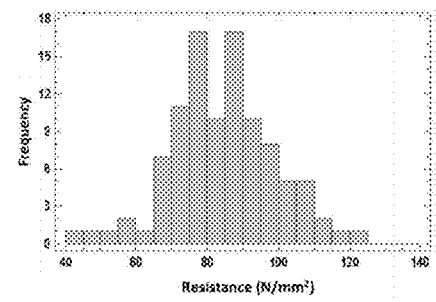
Tensile strength: Histogram
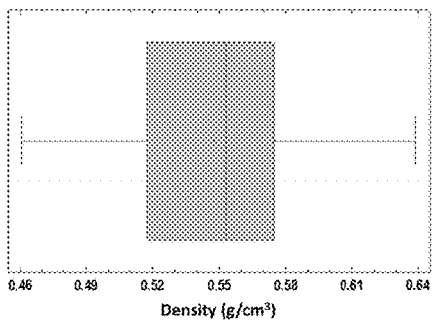
Density: Box-Cox Diagram
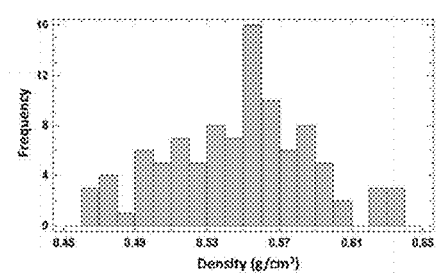
Density: Histogram
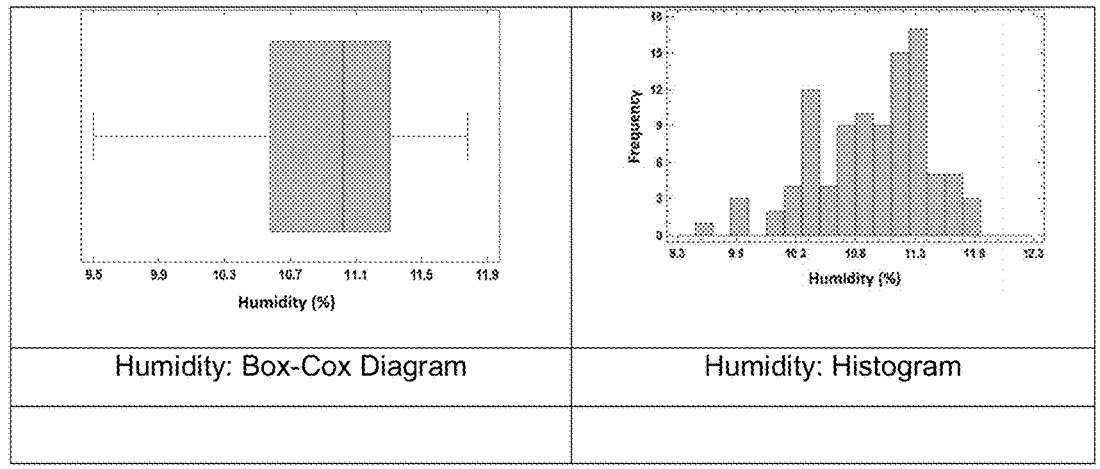
FIG. 12

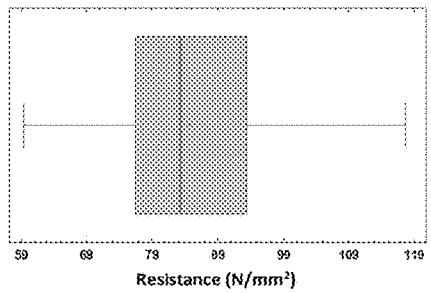
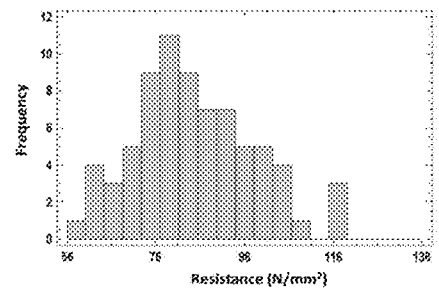
Tensile strength: Box-Cox Diagram | Tensile strength: Histogram
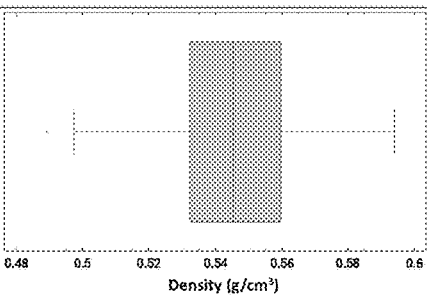
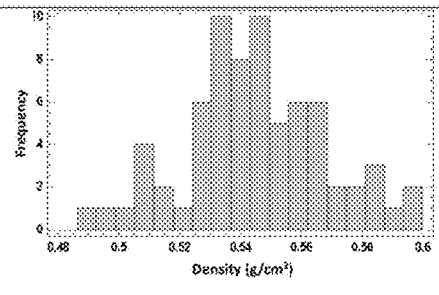
Density: Box-Cox Diagram | Density: Histogram
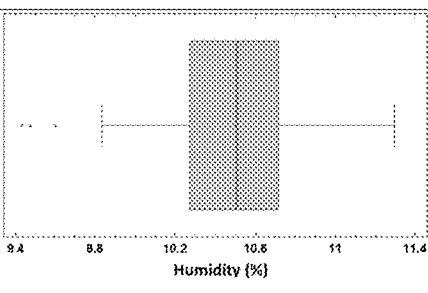
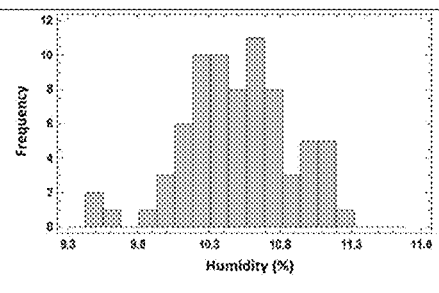
Humidity: Box-Cox Diagram | Humidity: Histogram
FIG. 13

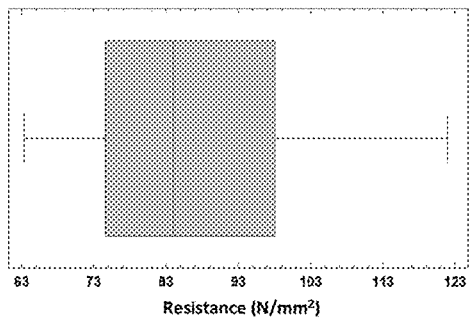
Tensile strength: Box-Cox Diagram
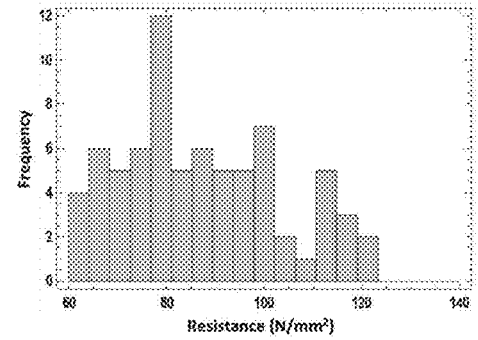
Tensile strength: Histogram
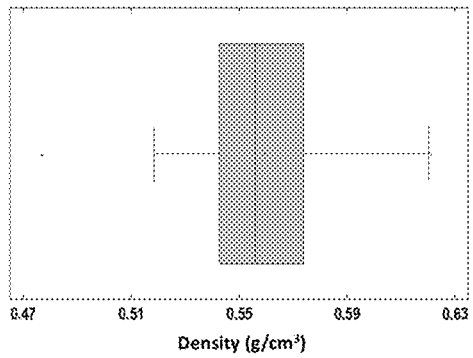
Density: Box-Cox Diagram
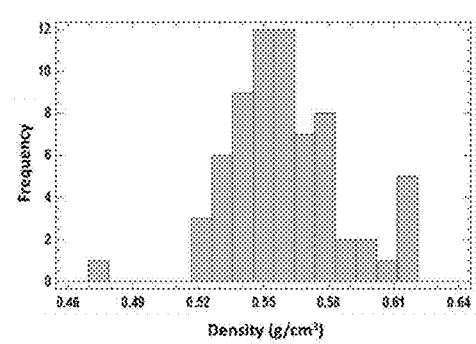
Density: Histogram
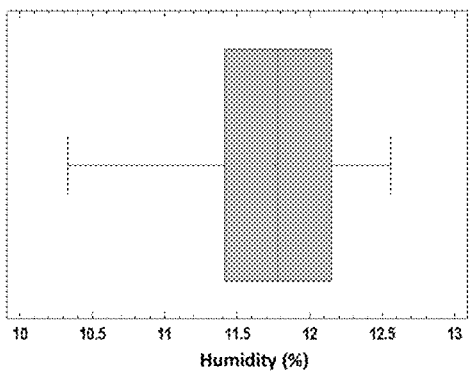
Humidity: Box-Cox Diagram
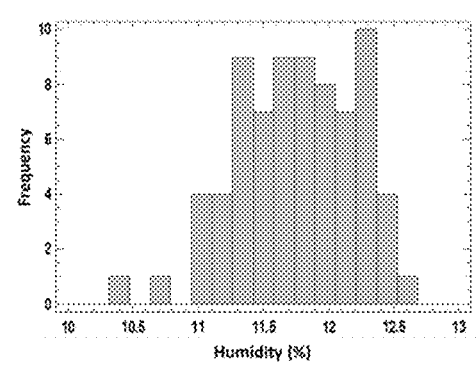
Humidity: Histogram
FIG. 14

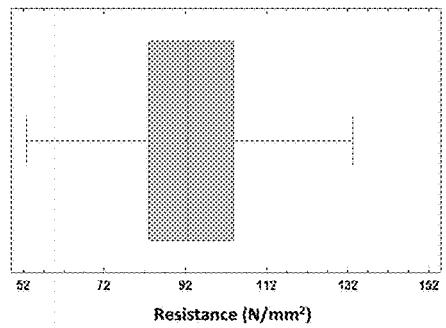
Tensile strength: Box-Cox Diagram
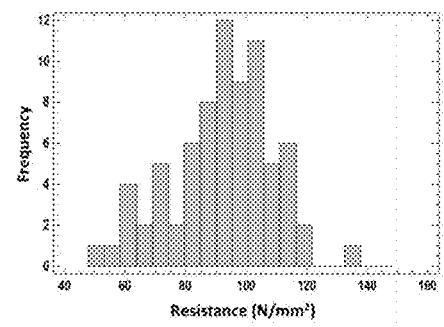
Tensile strength: Histogram
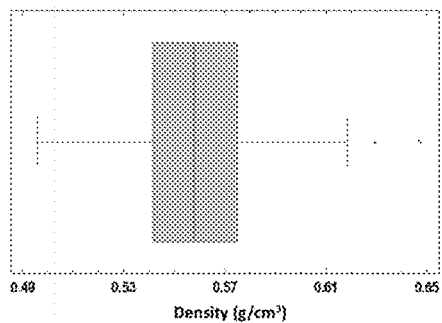
Density: Box-Cox Diagram
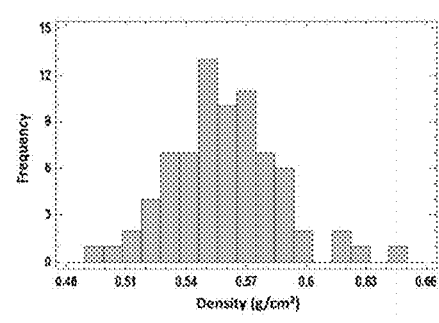
Density: Histogram
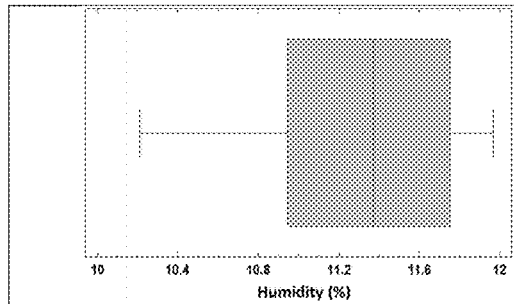
Humidity: Box-Cox Diagram
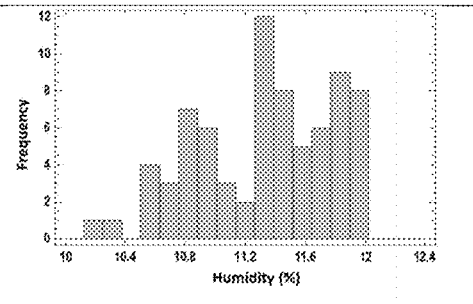
Humidity: Histogram
FIG. 15

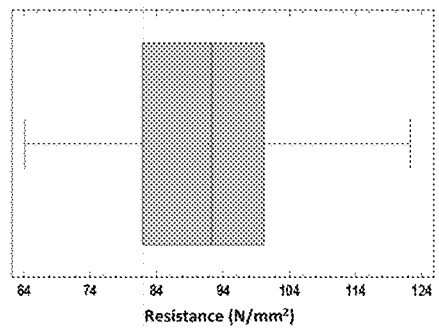
Tensile strength: Box-Cox Diagram
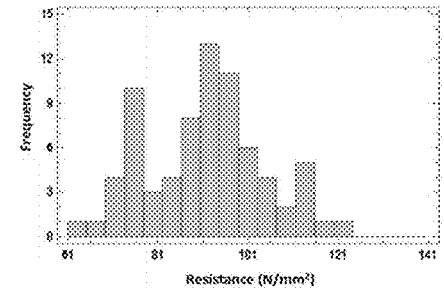
Tensile strength: Histogram
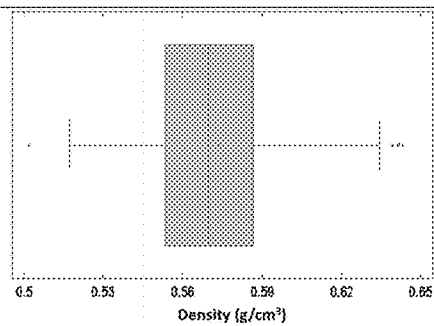
Density: Box-Cox Diagram
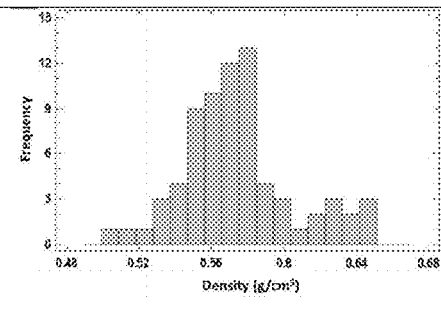
Density: Histogram
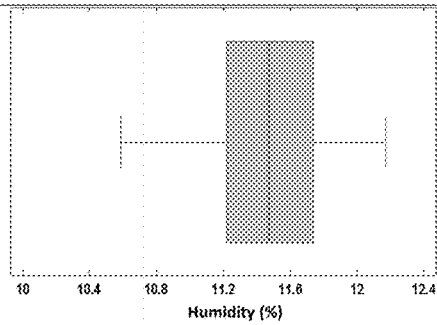
Humidity: Box-Cox Diagram
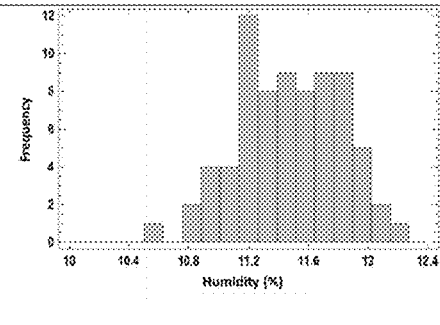
Humidity: Histogram
FIG. 16

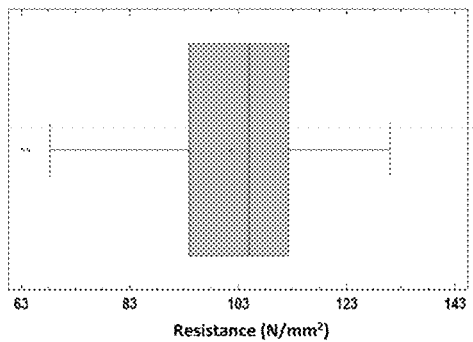
Tensile strength: Box-Cox Diagram
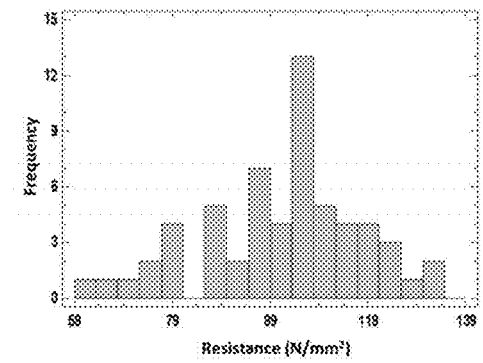
Tensile strength: Histogram
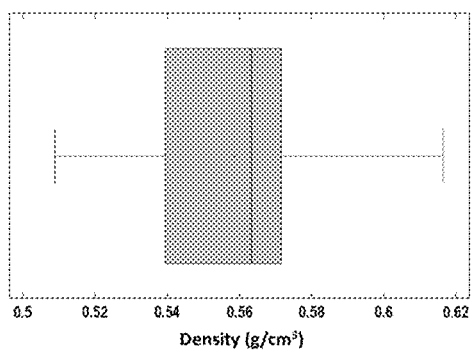
Density: Box-Cox Diagram
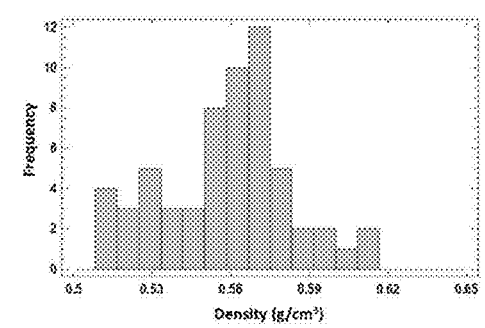
Density: Histogram
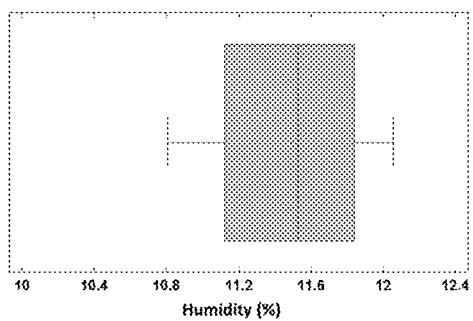
Humidity: Box-Cox Diagram
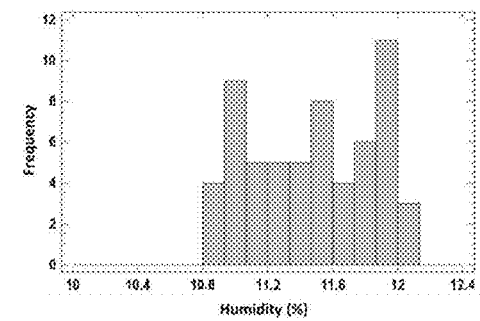
Humidity: Histogram
FIG. 17

PROCESS FOR REPAIRING DAMAGE TO WOOD AND RELATED CELLULOSIC PRODUCTS CAUSED BY TERMITES AND OTHER WOOD DAMAGING INSECTS

REFERENCE TO CROSS RELATED APPLICATIONS

This Continuation-In-Part application is based on U.S. Nonprovisional patent application Ser. No. 14/120,777, filed on Jun. 26, 2014, which is incorporated herein in their entirety.

SEQUENCE LISTING

The instant application contains a Sequence Listing which has been submitted electronically in ASCII format and is hereby incorporated by reference in its entirety. Said ASCII copy, created on Feb. 25, 2016, is named Termites_SL.txt and is 1,672 bytes in size.

FIELD OF THE INVENTION

The present invention embraces a biological system that can be used as bio-repair, insecticide, termiticide and bio-additive. This invention provides a biomaterial based in a bacteria that produces cellulose from sugar derivate. The biological system increases the resistance and flexural strength and also has an insecticide effect.

BACKGROUND OF THE INVENTION

Soil termites, also known as subterranean termites, are the most destructive termites in the United States. These insects, and other related insects can cause a lot of damage and should be controlled upon discovery.

Hundreds of thousands of termites in a colony well-organized among workers, soldiers and Queens tunnel 24 hours a day through soil and into the wooden frames of houses, fences and buildings providing new sources of cellulose for the entire colony.

If left untreated, termites can destroy the entire value of a home. According to the National Pest Management Association, termites are costing Americans more than $5 billion in damage each year. This is more than fire and floods combined. Destruction is boundless, because any home, regardless of design, can offer the ideal combination of heat, moisture and food for termites. In addition, many plans for housing are not covered by insurance for such damages. Without insurance protection, serious problems in selling a house may arise. Many lenders require a termite bond before lending money to homebuyers.

SUMMARY OF THE INVENTION

The present invention provides for the first time a biological system which provides the dual function of killing termites and other wood damaging insects while also producing a by-product substance having the capability of repairing damage by termites and other insects to wood and related cellulosic products.

In a particular embodiment of the present invention, a biological system, toxic to termites, is provided which produces a means by which damage caused by termites is repaired, said means comprising a by-product produced by a modification of the bacteria of the genus *Gluconacetobacter*. Preferably, the biological system is in the form of toxic bait.

In another embodiment of the present invention, a process is provided for killing termites and other wood damaging insects and for repairing damage to wood and related cellulosic products caused by termites comprising the steps of:
(a) Providing a modification of the bacteria of the genus *gluconacetobacter* toxic to termites and wood damaging insects, and insects family like acaridae and nematodes
(b) Converting said bacterial modification into a bait attractive to termites and other insects as a source of food;
(c) Allowing said bacterial modification to produce by-product ooze capable of repairing would damage by termites and other wood damaging insects.

The by-product ooze is toxic to termites and other insects and non-toxic to humans.

BRIEF DESCRIPTION OF THE DRAWINGS

FIG. 1. shows the 16S ribosomal RNA gene sequence of *Gluconacetobacter malus*.

FIG. 12 shows the different diagrams of Treatment 0
FIG. 13 shows the different diagrams of Treatment 1
FIG. 14 shows the different diagrams of Treatment 2
FIG. 15 shows the different diagrams of Treatment 3
FIG. 16 shows the different diagrams of Treatment 4ñ and:
FIG. 17 shows the different diagrams of Treatment 5

DETAILED DESCRIPTION OF THE INVENTION

Figure 2:
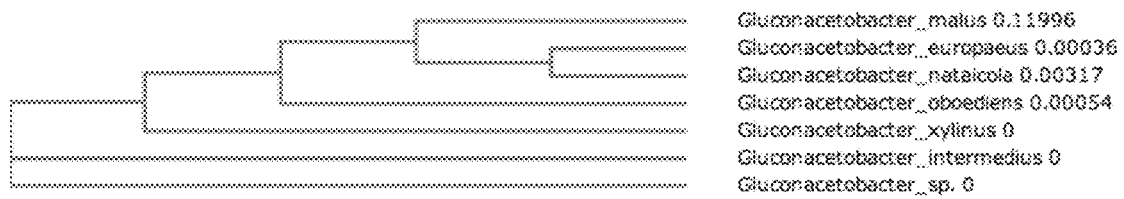
FIG. 2. illustrates the phylogenetic tree of 16S ribosomal RNA gene sequence of *Gluconacetobacter malus* with other species with high similarity.

A *Gluconacetobacter* bacterium from an apple was isolated. First, the apple was washed with distilled water and then it was crashed in 25 mL of sterile distilled water as well. The extract produced was incubated for 10 days at room temperature for the bacteria production. After this incubation, serial dilutions of the culture were done on LB agar plates and were incubated at 27-Celsius degrees for 2 days. The most diluted colonies corresponding to the white colored colonies were selected and analyzed by 16srRNA-PCR procedure using F8 forward primer (AGAGTTT-GATCCTGGCTCAG) and R1492 reverse primer (GGT-TACCTTGTTACGACTT) (Weisburg et al., 1991; Baker et al., 2003). The sequence obtained (FIG. 1) was analyzed by BLAST and had 92% of identity with *Gluconacetobacter intermedius* (gi: 594191428), *Gluconacetobacter xylinus* (gi: 359803333), *Gluconacetobacter* sp. (gi: 323482039), *Gluconacetobacter oboediens* (gi: 359803727), *Gluconacetobacter europaeus* (gi: 380292627) and *Gluconacetobacter nataicola* (gi: 343200325). So, we called our bacteria strains as *Gluconacetobacter malus*. Also, a phylogenetic tree analysis using ClustalW2-Phylogeny program was performed (FIG. 2).

An evaluation of cellulose yield was done. *G. malus* was cultured in liquid mediums using different nutrient sources (glucose and sugar derivate) for 2 weeks at 27 Celsius-degrees without shaking (static culture) to produce cellulose. A cellulose yield of 128.8 g/L, 119 g/L, 111.9 g/L, 99.8 g/L and 94.9 g/L was produced by *G. malus*. From glucose, sugar beet derivates 1, 2, 3 and 4, respectively (shown in Table 1).

TABLE 1

Cellulose yield using different nutrient sources.

| Sugar Source | Cellulose Yield (gr cellulose/ml culture) | Cellulose Yield (gr cellulose/L culture) |
|---|---|---|
| Glucose | 0.13 | 128.8 |
| Sugar Beet Molasses 1 | 0.12 | 119 |
| Sugar Beet Molasses 2 | 0.11 | 111.9 |
| Sugar Beet Molasses 3 | 0.10 | 99.8 |
| Sugar Beet Molasses 4 | 0.09 | 94.9 |

EXAMPLE 1

Biological System as Bio-repair

To test the biological system as bio-repair, physical properties of these celluloses were assayed by doing a Dynamic Mechanic Analysis (DMA). Resistance and mechanical strength of cellulose are five times more in comparison with wood-cellulose.

Figure 3:
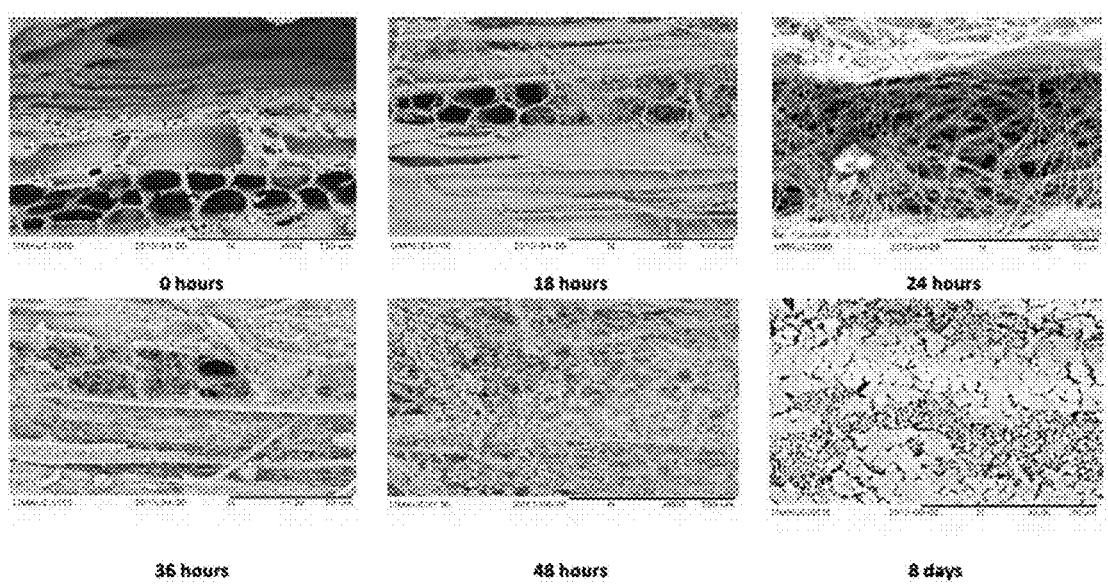
FIG. 3. shows the kinetic coverage of the cellulose adding the bacteria during the time.

Furthermore, electronic microphotographs shows how this biological system repairs and reconstitutes the damaged wood starting on the initial hours from its application to 8 days (FIG. 3). At 24 hours, a great quantity of cellulose's fibers can be shown. An efficient bio-repair process can be detected from 24 hours up to 8 days.

In USA there are 79.000.000 homes affected by termites. This biological product has a lot of advantages: is not toxic to the human, doesn't damage the environment and is a very effective as bio-repair product. It can be used as bio-repair on damaged wood's structures of homes caused by termites and other insects.

EXAMPLE 2

Biological System as Insecticide

Figure 4:
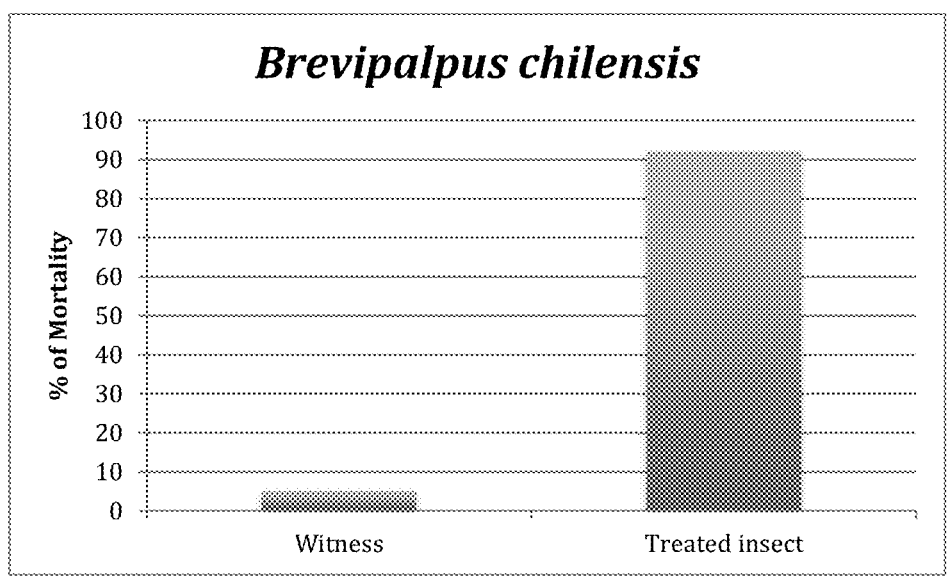
FIG. 4. shows the percentage of mortality of *Brevipalpus chilensis* with water (witness) and treated insect with culture supernatant (SN) of the bacterial cellulose culture. The SN was added to the privet leaves, not directly to the insect. After 7 days of post-treatment, the percentage of mortality was measured. This assay was performed using eggs and mobile insects. Each assay was done 10 times.

To evaluate the insecticidal effect, an aliquot of the supernatant from bacterial cellulose cultures was settled on a plate with a coleopteran to emulate the natural environmental conditions. When the coleopteran reaches the supernatant, the insect dies. Contrary to when the insect eats the bacterial cellulose. These assays were performed using *Brevipalpus chilensis* (a mite that infects vine plants). The SN was added to the privet leaves, not directly to the insect. After 7 days of post-treatment, we measured the percentage of mortality. A 92% of mortality was shown using the SN of the bacterial cellulose culture (FIG. 3). Also, the same assay was done, but using a 1/10 dilution of the SN (FIG. 4). We detected a 73% of mortality. So, the diluted SN is very effective.

Figure 5:
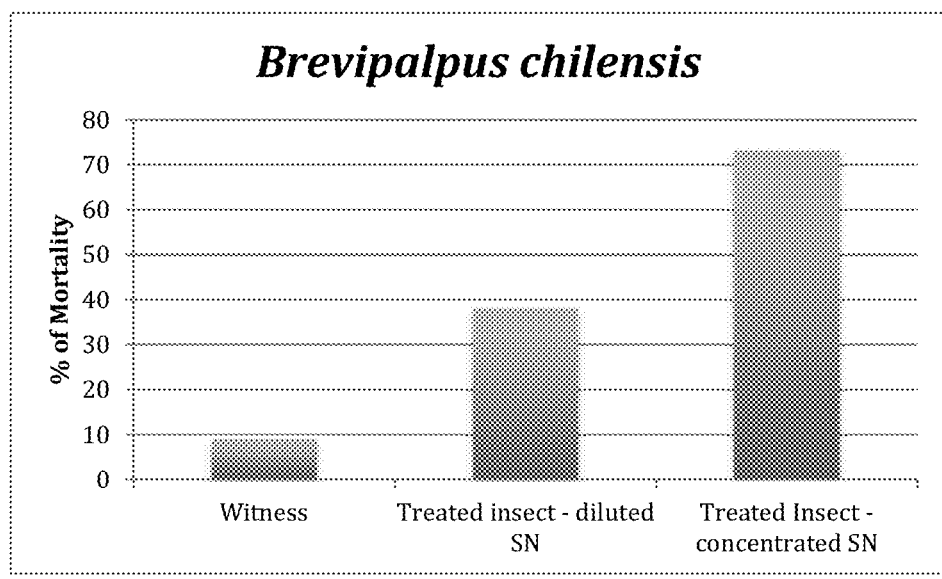
FIG. 5. Shows the percentage of mortality of *B. chilensis* using water (witness), diluted supernatant (diluted SN) and concentrated SN (direct SN of bacterial cellulose culture). The assay was done as in FIG. 3.
Figure 6:
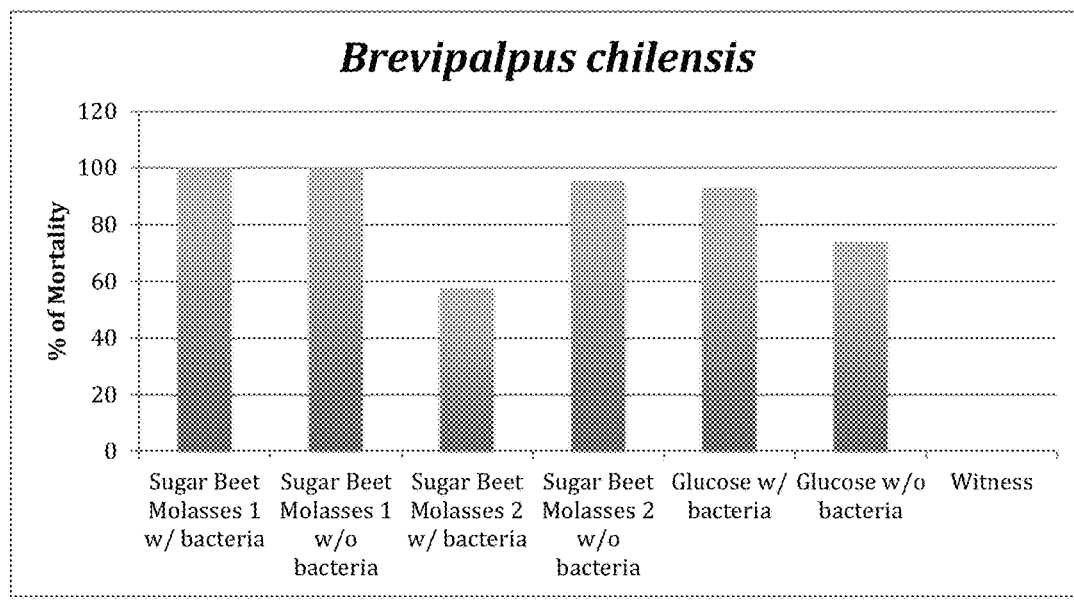
FIG. 6. shows the percentage of mortality of *B. chilensis* using supernatant (SN) of bacterial cellulose culture using different nutrient sources (sugar beet derivates 1 and 2, and glucose) with or without bacteria (treated with 0.1 N NaOH). The assay was done as in FIG. 3.

Furthermore, a similar assay was performed using SN from bacterial cellulose cultures with different nutrient source. We determined that the different SNs were effective (FIG. 5). Also, the same treatment was done with and without bacteria (SN with 0.1N NaOH). We saw activity in both treatments. We conclude that the toxin is in the bacterial cellulose supernatant.

In the *vinifera* vine sprouting in early may cause tissue necrosis and death cause of outbreaks and also, dehydration rachis, pedicels and bronzing of leaves.

On the other hand, we test the insecticidal effect using 9 nematodes (Table 2). Nematodes-based termite s are phytoparasitic of a wide of vegetable cultivation like tomato and also vine plants. In this assay we use the SN (filtrated or not) of the liquid culture using Sugar Beet Derivate 1 as carbon source. All the insects die using the SN. Water added to the nematodes was used as negative control. The SN is effective against different types of insects.

TABLE 2

Insecticidal effect of Supernatant using Sugar Beet Molasses as nutrient sources

| Dilution | Filtrated | Not Filtrated | Water |
|---|---|---|---|
| 1 Supernatant/ 9 nematodes | 9 nematodes died | 9 nematodes died | 9 nematodes alive |
| 5 Supernatant/ 5 nematodes | 5 nematodes died | 5 nematodes died | 5 nematodes alive |

This biological product can be used as insecticide, mostly important as a termiticide to protect the wood structures from termites while this product is repairing the damaged wood as mentioned before. Also, can be used in the agriculture, mainly in the countries that are susceptible to insect damage by mites and other insects. This new biological compound shows a great potential to control the damage of *Brevipalpus chilensis* in our *Vitis vinifera*. The actually acaricides are not sufficient effective to control this mite.

EXAMPLE 3

Biological System as Bio-additive

The biological compound can be used in the fabrication of added-resistance laminated and agglomerated wood panels. Plywood increases over 5 times its resistance to flexion.

In 2011, the International Agency for Research on Cancer (IARC) classifies the formaldehyde as carcinogenic agent, based on epidemiologic studies of cancer in animals and humans. The new biological compound can replace the formaldehyde to a polymer that catalyzes the dry and reduces the use of matchwood for the Eco-wood formulation, using materials that aren't toxic on humans.

Below, a report to determine the tensile strengths of wood veneers treated with the composition of the present invention and to analyze any possible influences treatment on tensile strength is included.

Report on the Tensile Strength of Wood Veneers Treated with Wood Eagleone

1.—Background.

The following report by the Laboratory of Wood Technology (Laboratorio de Tecnologia de la Madera) of the Technical School of Rural Engineering (Escuela Técnica Superior de Ingenieros de Montes) at the Universidad Politécnica de Madrid.

2.—Testing Regulations.

Testing methods were created in compliance with the following regulations:

UNE-EN 314-1:2007. Plywood. Bonding quality. Part 1: Test methods.

UNE-EN 13183-1:2002, UNE-EN 13183-1:2003 Erratum, UNE-EN 13183-1/AC:2004. Moisture content of a piece of sawn timber—Part 1: Determination by oven drying.

UNE 56.531:1977. Physical-mechanical characteristics of wood. Determination of specific weight.

3.—Operational Procedure.

Wood specimens were prepared between Apr. 13, and 15, 2015, in the Laboratory of Wood Technology (Laboratorio de Tecnologia de la Madera) of the Technical School of Rural Engineering (Escuela Técnica Superior de Ingenieros [E.T.S.I.] de Montes). Specimens were prepared with pinewood veneer originating from the southeast United States. Overall, 470 specimens (150×23×0.65 mm) were prepared, of which, 110 (i.e. 100 specimens for assays and 10 as reserves) remained at the Laboratory of Wood Technology as a reference standard (treatment 0).

As requested by the client, the remaining samples (360 specimens) were sent on May 19$^{th}$ to the company Creative BioScience at Avda. del Valle Norte 857, Of 102, Ciudad Empresarial, Santiago, Chile. The specimens were divided into three groups for posterior testing with three distinct WOOD EAGLEONE treatments (100 specimens per assay and 20 reserve specimens for each treatment). To best homogenize variations in the wood, specimens were randomly distributed among the treatment groups.

The specimens sent to Creative BioScience were initially going to be subjected to three distinct WOOD EAGLEONE treatment assays, but five treatments were finally test. According to information provided by Mrs. Adda Mora Foppiano, the number of specimens used for each treatment assay was as follows:

| Treatment | No. of Specimens |
| --- | --- |
| Treatment 0 (standard) - E.T.S.I. Montes | 100 |
| Treatment 1 - Creative BioScience | 75 |
| Treatment 2 - Creative BioScience | 75 |
| Treatment 3 - Creative BioScience | 75 |
| Treatment 4 - Creative BioScience | 75 |
| Treatment 5 - Creative BioScience | 60 |

On Sep. 24, 2015, the samples treated by Creative BioScience were received by the Laboratory of Wood Technology.

Before assays, the specimens were conditioned until reaching a constant mass in a climatic chamber at 20±2° C. and 65±5% relative humidity.

Prior to tensile strength tests, specimen densities (ρ) were calculated according to the following formula:

$$\rho = \frac{p}{a \cdot b \cdot t}$$

ρ: density (g/cm$^3$)
p: specimen weight (g)
t: specimen thickness (cm)
a: specimen length (cm)
b: specimen width (cm)

Figure 7:
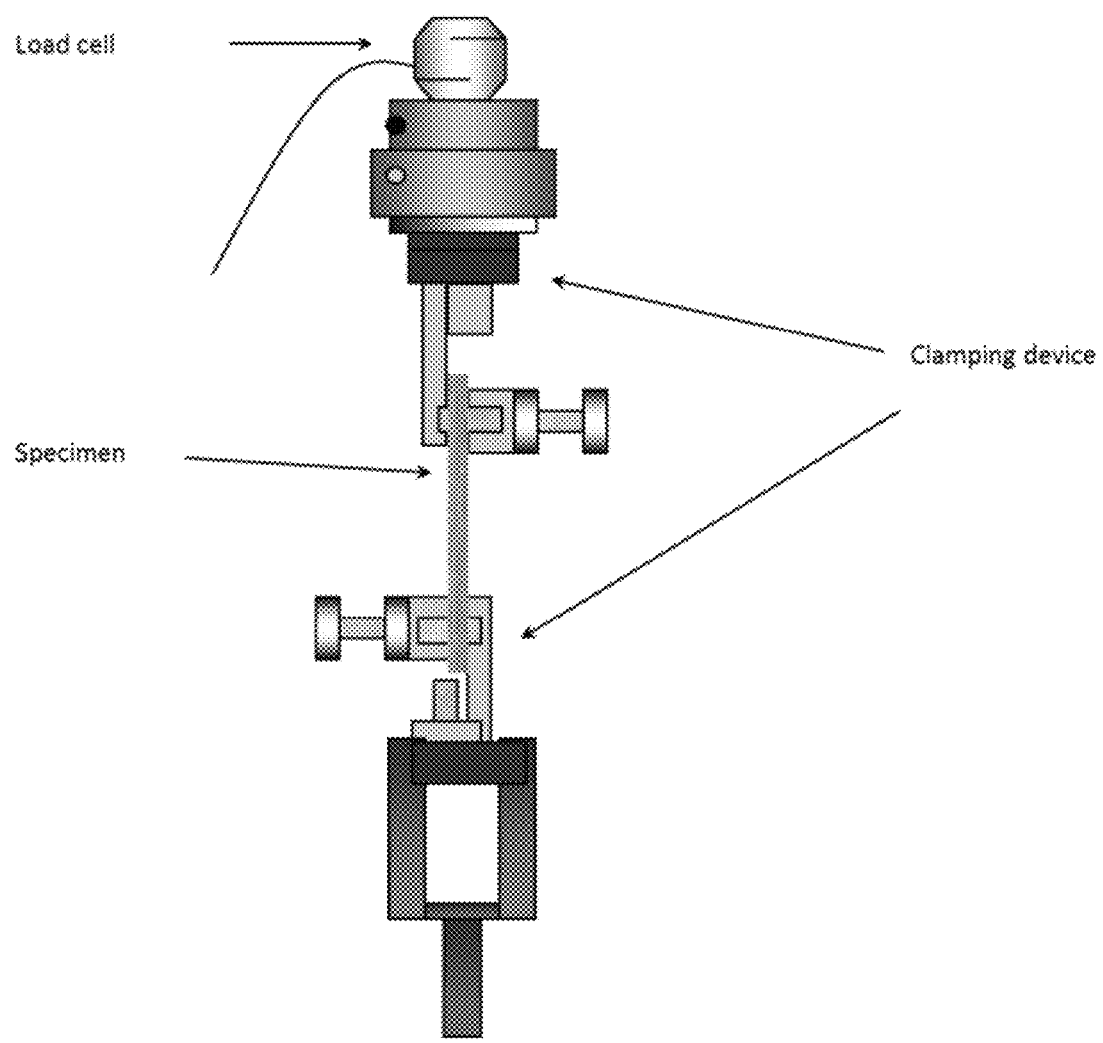
FIG. 7 shows the universal testing machine used to check tensile strengths of the veneer specimens.
Figure 8:
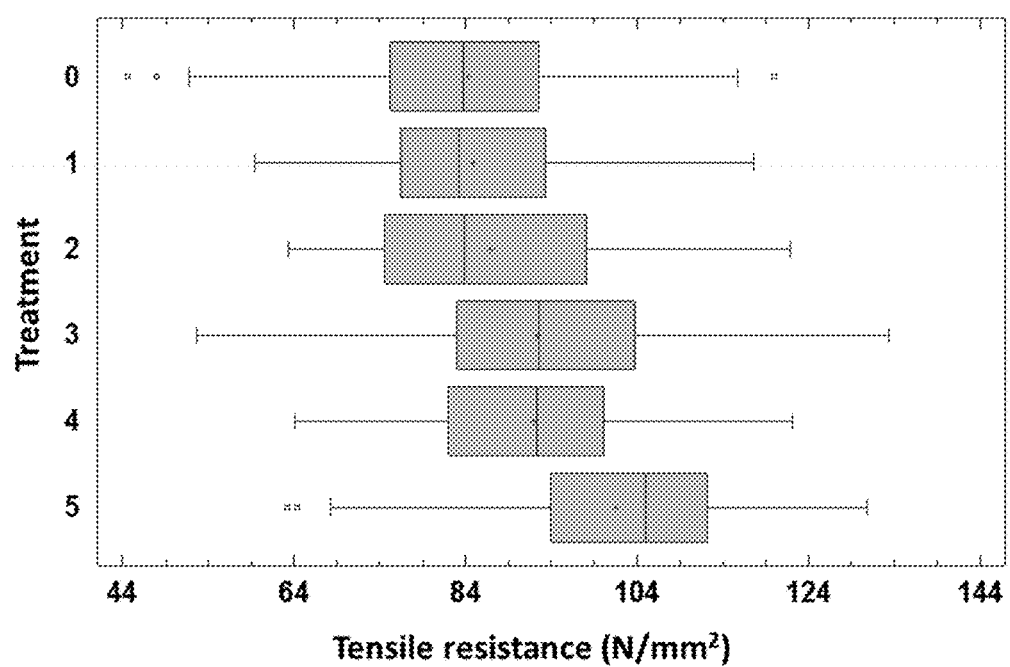
FIG. 8 shows a Box-Cox diagram for all treatments
Figure 9:
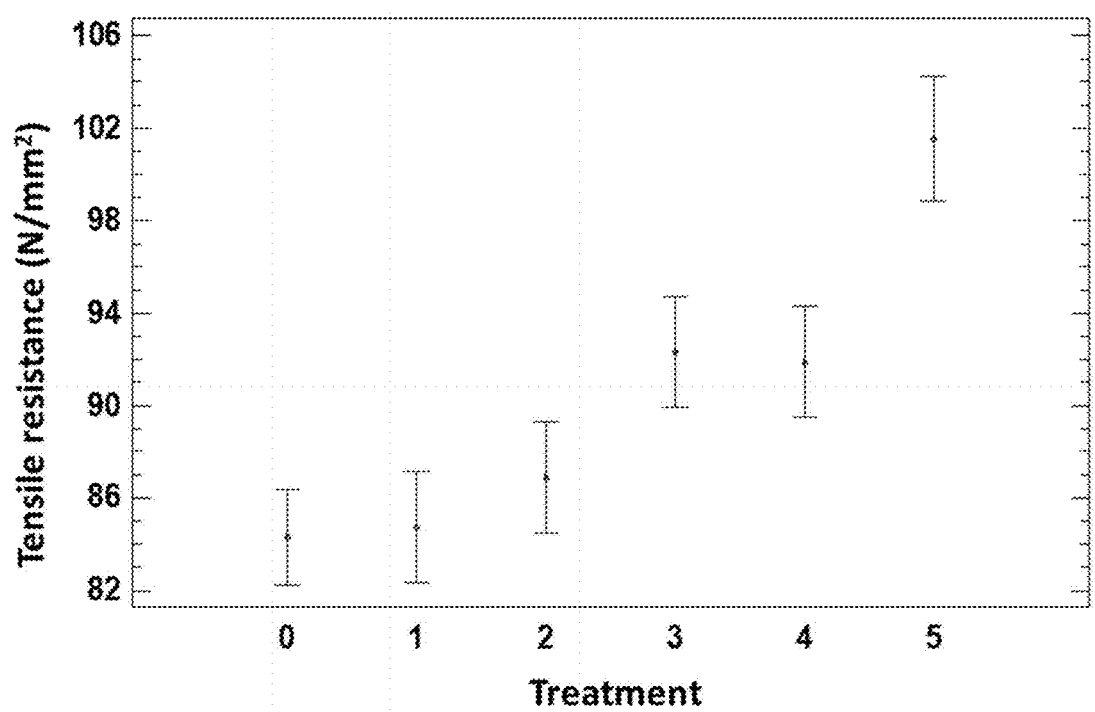
FIG. 9 shows a diagram of Fisher's LSD intervals.
Figure 10:
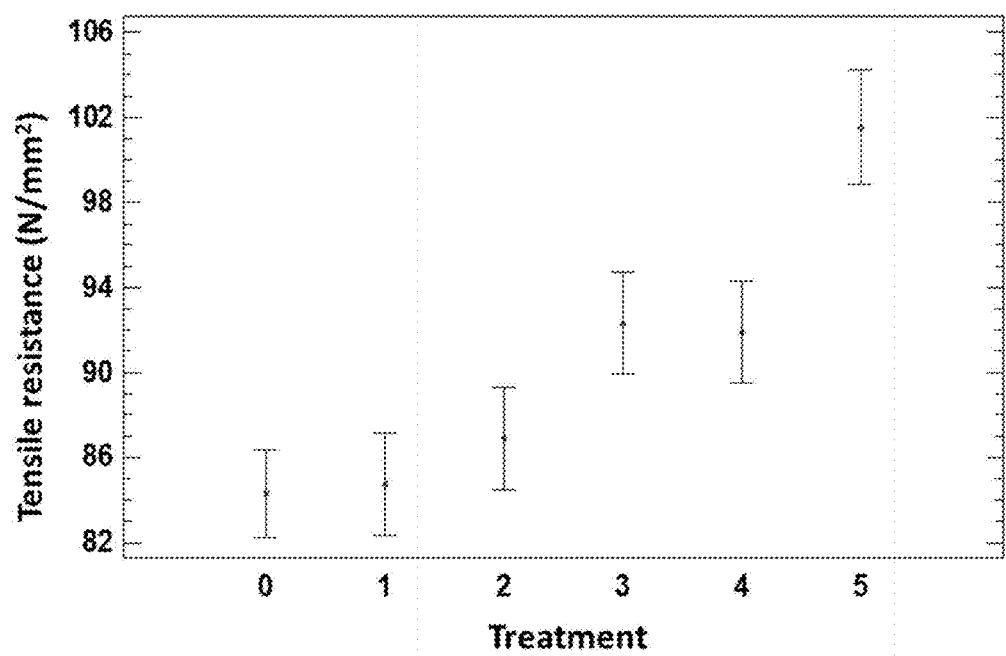
FIG. 10 shows a diagram of Scheffé intervals.
Figure 11:
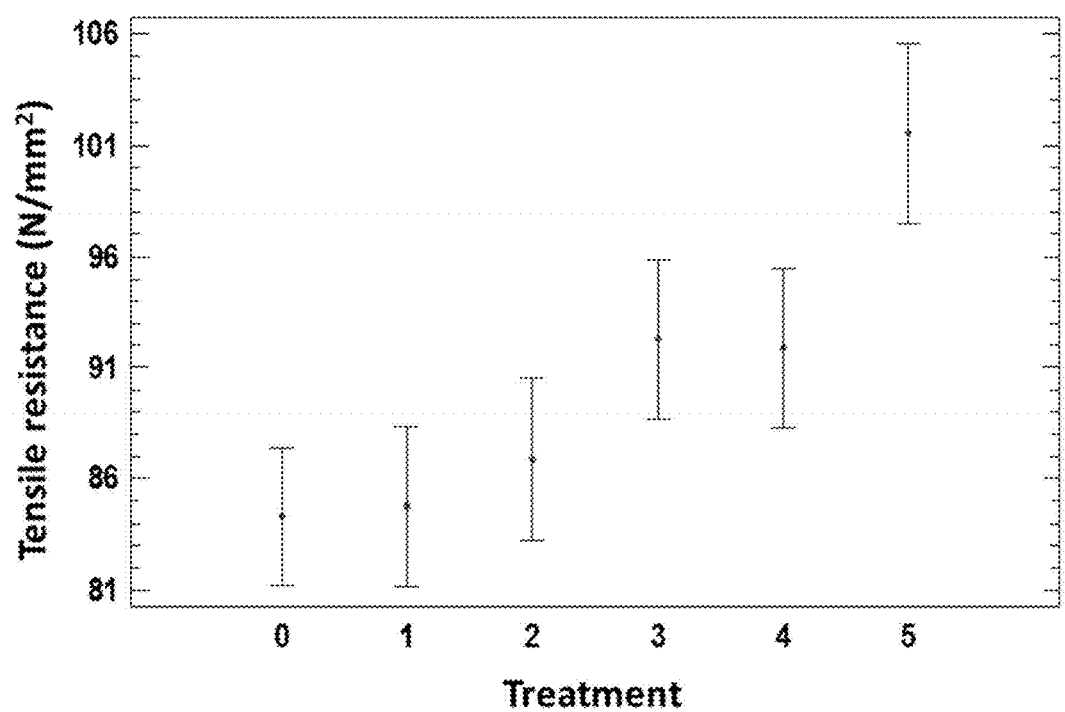
FIG. 11 shows a diagram of Bonferroni intervals.

The tensile strengths of the veneer specimens were determined with a universal testing machine (Class 0.5 load cell, 5 kN capacity). (See FIG. 7).

The tensile strength (k) of each specimen was calculated according to the following formula:

$$f_v = \frac{F}{b \cdot t}$$

$f_v$: tensile strength (N/mm$^2$)
F: ultimate load of the specimen (N)
t: specimen thickness (mm)
b: specimen width (mm)

Once the tensile strength test was concluded, the humidity (h) of each specimen was calculated according to the following formula:

$$h \% = 100 \cdot \frac{p_h - p_0}{p_0}$$

h: humidity (%)
$p_h$: wet weight (g)
$p_0$: dry weight (g)

The mean and standard deviation were calculated for all results.

An analysis of variance (ANOVA) with a 95% confidence interval was used to detect possible significant differences between the applied treatments.

Prior to ANOVA assessments, data were tested for assumptions of normality, independence, and homoscedasticity against bias. Additionally, kurtosis was determined, and the Lavene's Test was applied.

The Grubbs' test was applied to all properties to detect outliers in the dataset. Each datum considered a statistical outlier was individually assessed to evaluate possible elimination from the dataset.

In cases where statistical differences were detected, confidence intervals were assessed to establish between which treatments such differences existed. These assessments were carried out using the Fisher's Least Significant Difference (LSD), Scheffé, and Bonferroni tests, thereby minimizing the effect of sample size.

Fisher's LSD test is the method that detects the most significant differences and is highly efficient in detecting real differences between means. However, this method is not very conservative and is not adequate for evaluating a high number of treatments, particularly since type I errors (i.e. rejection of the hypothesis when there are no significant differences) increase with the number of treatments.

In turn, the Scheffé test does not require an equilibrated design; in other words, this test does not need the same quantity of samples in each treatment, as in the present case.

Furthermore, the Scheffé analysis is one of the most robust mean comparison tests and presents fewer type 1 errors.

Finally, the Bonferroni test is an adequate method when the number of comparisons is not very high. This method is more conservative than the Scheffé test and is better than Fisher's LSD test at controlling for type I errors.

For additional data confirmation, bootstrapping was used to obtain the confidence intervals for the tensile strength ratios of each treatment. This robust numerical method does not assume previous conditions of normality and homoscedasticity, which are required for the other performed analyses. The inclusion of the unit within the indicated confidence interval indicates that significant differences do not exist between the assessed strengths.

Descriptive statistical analyses, ANOVA, and confidence interval assessments were performed using the STATGRAPHICS Centurion XVI v.16.2.04 program. To obtain the confidence intervals of the tensile strength ratios, the MATLAB R2013b program was used. All statistical analyses were performed considering a 95% confidence interval.

4.—Results.

4.1.—Tensile Strength Data for Each of the Treatments ($N/Mm^2$).

| Treatment | No. of Data Points | Mean | Standard Deviation | Skewness | Kurtosis |
|---|---|---|---|---|---|
| 0 | 100 | 84.30 | 14.33 | −0.27 | 0.65 |
| 1 | 75 | 84.74 | 13.45 | 1.36 | −0.41 |
| 2 | 75 | 86.87 | 15.94 | 1.73 | −1.19 |
| 3 | 75 | 92.29 | 16.59 | −1.45 | −0.05 |
| 4 | 75 | 91.90 | 12.98 | 0.34 | −0.87 |
| 5 | 60 | 101.52 | 16.11 | −1.44 | −0.16 |

All bias and kurtosis values were within the interval (−2, 2), corresponding to normal distribution. Therefore, the hypothesis that property data originate from a normal distribution cannot be discarded.

Each statistically determined outlier was individually assessed, and none presented technical reasons warranting elimination from the global dataset.

4.2.—Verification of Variance.

|  | p-value |
|---|---|
| Lavene's Test | 0.19 |

Since the p-value was greater than 0.05, no significant differences existed between the detected variances (95% confidence interval).

4.3.—Anova.

| Source | SS | DF | MS | F ratio | p-value |
|---|---|---|---|---|---|
| Inter-treatment | 14426.6 | 5 | 2885.32 | 13.01 | <0.01 |
| Intra-treatment | 99815.0 | 450 | 221.81 | | |
| Total | 114242 | 455 | | | |

Abbreviations:
SS, sum of squares;
DF, degree of freedom;
MS, mean square

Since the p-value was less than 0.05, significant differences existed between the distinct sample treatments (95% confidence interval).

4.4.—Fisher's LSD Intervals.

| Treatment | Lower Limit ($N/mm^2$) | Upper Limit ($N/mm^2$) | Group |
|---|---|---|---|
| 0 | 82.23 | 86.37 | A |
| 1 | 82.34 | 87.15 | A |
| 2 | 84.47 | 89.28 | A |
| 3 | 89.90 | 94.68 | B |
| 4 | 89.49 | 94.30 | B |
| 5 | 98.83 | 104.21 | C |

Note:
Distinct letters for groups indicate significant differences (95% confidence interval).

Considering a 95% confidence interval, significant differences did not exist between treatments 0, 1, and 2 or between treatments 3 and 4. However, significant differences did exist between treatment 5, treatment group [0, 1, and 2], and treatment group [3 and 4].

4.5.—Scheffé Intervals.

| Treatment | Lower Limit ($N/mm^2$) | Upper Limit ($N/mm^2$) | Group |
|---|---|---|---|
| 0 | 80.78 | 87.82 | A |
| 1 | 80.66 | 88.84 | AB |
| 2 | 82.78 | 90.96 | AB |
| 3 | 88.23 | 96.36 | B |
| 4 | 87.80 | 95.99 | AB |
| 5 | 96.94 | 106.11 | C |

Note:
Distinct letters for groups indicate significant differences (95% confidence interval).

Significant differences existed between treatment 5 and the remaining treatments, as well as between treatments 0 and 3. However, no significant differences existed between the treatment group [1, 2, and 4] and treatment 0 or treatment 3.

4.6.—Bonferroni Intervals.

| Treatment | Lower Limit ($N/mm^2$) | Upper Limit ($N/mm^2$) | Group |
|---|---|---|---|
| 0 | 81.19 | 87.41 | A |
| 1 | 81.13 | 88.36 | AB |
| 2 | 83.26 | 90.48 | ABC |
| 3 | 88.71 | 95.88 | C |
| 4 | 88.28 | 95.51 | BC |
| 5 | 97.48 | 105.57 | D |

Note:
Distinct letters for groups indicate significant differences (95% confidence interval).

Significant differences existed between treatment 5 and the remaining treatments, as well as between treatment 0 and treatment group [3 and 4]. However, significant differences did not exist between treatments 0, 1, and 2; between treatments 2, 3, and 4; or between treatments 1, 2, and 4.

4.7.—Ratios Between Tensile Strengths According to Treatment.

The following table provides the tensile strength ratios obtained following each of the distinct treatments.

|  |  | Treatment | | | | | |
|---|---|---|---|---|---|---|---|
|  |  | 0 | 1 | 2 | 3 | 4 | 5 |
| Treatment | 0 | — | 1.00 (0.95-1.04) | 0.97 (0.92-1.02) | 0.91 (0.87-0.96) | 0.92 (0.88-0.96) | 0.83 (0.80-0.87) |
|  | 1 | 1.00 (0.96-1.05) | — | 0.98 (0.93-1.02) | 0.92 (0.88-0.96) | 0.92 (0.89-0.96) | 0.83 (0.80-0.87) |
|  | 2 | 1.03 (0.99-1.08) | 1.03 (0.98-1.07) | — | 0.94 (0.90-0.99) | 0.95 (0.90-0.99) | 0.86 (8.82-0.90) |
|  | 3 | 1.09 (1.04-1.14) | 1.09 (1.04-1.14) | 1.06 (1.01-1.11) | — | 1.00 (0.96-1.05) | 0.91 (0.86-0.95) |
|  | 4 | 1.09 (1.05-1.13) | 1.08 (1.04-1.13) | 1.06 (1.01-1.11) | 1.00 (0.96-1.05) | — | 0.91 (0.87-0.94) |
|  | 5 | 1.20 (1.15-1.26) | 1.20 (1.15-1.26) | 1.17 (1.11-1.23) | 1.10 (1.05-1.16) | 1.10 (1.06-1.16) | — |

Note:
In bold are the confidence intervals that did not include the unit, indicating the existence of significant differences.

Significant differences were detected between treatment 5 and the remaining treatments, as well as between treatment group [0, 1, and 2] and treatment group [3 and 4]. However, no significant differences were detected between treatments 0, 1, and 2 or between treatments 3 and 4.

5.—Discussion.

The obtain tensile strength data met assumptions of normality and equality of variance. Consequently, ANOVA-based methods were acceptable for studying the influence of treatments on the tensile strength of samples.

A precursory evaluation of the data would indicate the existence of three groups within the treatments. The first group would be comprised by treatments 0 (standard), 1, and 2. The second group would be comprised by treatments 3 and 4, and the third group would be exclusively comprised of treatment 5.

Nevertheless, extended evaluation reveals that such group delineations are not so clear. What can be confirmed is the existence of significant differences between treatments 0, 3, and 5, with all analyses (i.e. Fisher's LSD, Scheffé, Bonferroni, and tensile strength ratios) arriving to this same conclusion. These differences indicate increased tensile strengths of 9.47% between treatments 0 and 3, of 20.42% between treatments 0 and 5, and of 10.00% between treatments 3 and 5.

Similarly, significant differences were confirmed by all analyses (i.e. Fisher's LSD, Scheffé, Bonferroni, and tensile strength ratios) between treatments [1 and 5], [2 and 5], and [4 and 5]—The determined increases in tensile strength for these treatments were 19.80%, 16.86%, and 10.46%, respectively.

While differences existed between treatments 1 and 3, indicating the existence of distinct groups, these results must be interpreted with caution. Although the intervals for Fisher's LSD, Bonferroni, and tensile strength ratio tests showed significant differences, this result was not obtained by Scheffé interval analysis. In particular, the Scheffé test indicated that the upper confidence interval limit of treatment 1 (88.84 N/mm$^2$) overlaps with the lower confidence interval limit of treatment 3 (88.23 N/mm$^3$).

This same situation, albeit more pronounced, occurred between treatments 2 and 3, where significant differences were found by the Fisher's LSD and tensile strength ratio analyses but not by the confidence intervals obtained in the Bonferroni and Scheffé tests.

Regarding treatment 4, although significant differences were found with treatments 3 and 5, the same cannot be definitively said for the remaining treatments. On the one hand, confidence interval analysis for the Fisher's LSD and tensile strength ratio tests revealed significant differences with treatments 0, 1, 2, and 5. On the other hand, analysis of the Bonferroni confidence intervals only resulted in significant differences with treatments 0 and 5. Similarly, the Scheffé confidence intervals only showed significant differences with treatment 5.

The uncertainty caused by analysis-dependent variations in confidence interval overlapping, or lack thereof, between treatments could be due to a lack of data normality or an insufficient number of data points. As previously mentioned, the coefficients of skewness and kurtosis were within the interval expected for normal distribution. Considering this, it is more likely that above mentioned uncertainties are the result of insufficient data points, an issue that could have been aggravated by the lack of an equilibrated assay design (i.e. the number of assessed specimens varied between treatments).

6.—Conclusions.

1. No significant differences existed between treatments [0 and 1], [0 and 2], [1 and 2], or [3 and 4].
2. Treatment 0 presented significant differences with treatments 3 and 5.
3. Treatment 1 presented significant differences with treatment 5.
4. Treatment 2 presented significant differences with treatment 5.
5. Treatment 3 presented significant differences with treatments 0 and 5.
6. Treatment 4 presented significant differences with treatment 5.
7. Treatment 5 presented significant differences with all other treatments, indicating in all cases an increased tensile strength.
8. The existence or lack of significant differences cannot be confirmed between treatments [0 and 4], [1 and 3], [1 and 4], [2 and 3] or [2 and 4].
9. A larger dataset and equilibrated assay design could resolve some of the presented uncertainties.

Assay Results

Treatment 0—Standard

| Property | No. of Data Points | Mean | Standard Deviation | Skewness | Kurtosis |
|---|---|---|---|---|---|
| Tensile strength ($N/mm^2$) | 100 | 84.30 | 14.33 | −0.27 | 0.65 |
| Specific Density ($g/cm^3$) | | 0.548 | 0.041 | −0.18 | −0.62 |
| Humidity (%) | | 10.9 | 0.5 | −1.95 | −0.10 |

Treatment 1

| Property | No. of Data Points | Mean | Standard Deviation | Skewness | Kurtosis |
|---|---|---|---|---|---|
| Tensile strength ($N/mm^2$) | 75 | 84.74 | 13.45 | 1.36 | −0.41 |
| Specific Density ($g/cm^3$) | | 0.545 | 0.023 | −0.07 | −0.12 |
| Humidity (%) | | 10.5 | 0.4 | −1.40 | 0.70 |

Treatment 2

| Property | No. of Data Points | Mean | Standard Deviation | Skewness | Kurtosis |
|---|---|---|---|---|---|
| Tensile strength ($N/mm^2$) | 75 | 86.87 | 15.94 | 1.73 | −1.19 |
| Specific Density ($g/cm^3$) | | 0.559 | 0.026 | 0.94 | 1.74 |
| Humidity (%) | | 11.8 | 0.5 | −1.36 | 0.15 |

Treatment 3

| Property | No. of Data Points | Mean | Standard Deviation | Skewness | Kurtosis |
|---|---|---|---|---|---|
| Tensile strength ($N/mm^2$) | 75 | 92.29 | 16.59 | −1.45 | −0.05 |
| Specific Density ($g/cm^3$) | | 0.559 | 0.027 | 1.77 | 1.90 |
| Humidity (%) | | 11.3 | 0.5 | −1.48 | −1.30 |

Treatment 4

| Property | No. of Data Points | Mean | Standard Deviation | Skewness | Kurtosis |
|---|---|---|---|---|---|
| Tensile strength ($N/mm^2$) | 75 | 91.90 | 12.98 | 0.34 | −0.87 |
| Specific Density ($g/cm^3$) | | 0.574 | 0.031 | 1.86 | 0.42 |
| Humidity (%) | | 11.5 | 0.3 | −0.42 | −0.67 |

Treatment 5

| Property | No. of Data Points | Mean | Standard Deviation | Skewness | Kurtosis |
|---|---|---|---|---|---|
| Tensile strength ($N/mm^2$) | 60 | 101.52 | 16.11 | −1.44 | −0.16 |
| Specific Density ($g/cm^3$) | | 0.559 | 0.025 | 0.12 | −0.25 |
| Humidity (%) | | 11.5 | 0.4 | −0.43 | −1.95 |

What is claimed is:

1. A process for repairing damage to wood caused by termites and other wood damaging insects comprising the steps of:
   (a) providing a modification of *gluconacetobacter malus* toxic to termites and other wood damaging insects;
   (b) converting said *gluconacetobacter malus* into a bait attractive to termites and other wood damaging insects as a source of food;
   (c) allowing said *gluconacetobacter malus* to produce a by-product ooze which is then used to repair in situ wood damaged by termites and other wood damaging insects.

2. The process according to claim 1, wherein said by-product ooze is toxic to termites and other wood damaging insects and non-toxic to humans.

* * * * *

SEQUENCE LISTING

```
<160> NUMBER OF SEQ ID NOS: 1

<210> SEQ ID NO 1
<211> LENGTH: 1000
<212> TYPE: DNA
<213> ORGANISM: Komagataeibacter xylinus

<400> SEQUENCE: 1
gtgtagttaa gttttacaa tacaagtcgc acgatctttt cgggtttagt ggcggacggg      60
tgagtaacgc gtagggattt atccacgggt ggggaataat tttggaaaac tgaagctaat     120
cccgcatgac acctgagggt caaaggcgca agtcccctgt ggagaaacct gctttcaatt     180
```

-continued

```
acctagttgg gggggtaaag gcctaccaag gcaatgatca atagctggtc tgagaggatg    240
atcacccaca ctgggactga aacacggccc aaactcctac gggaggcagc agtgggaaat    300
attgaacaat gggcgcaacc ctgatccacc aatgccgcgt gtgtgaaaaa ggttttcgga    360
ttgtaaagca ttttcagcgg ggacaatgat gacggtcccc gcaaaaaaac ccccggctaa    420
tttcgtgcca gcacccgcgg taatacaaag ggggcaagcg ttgctcgaaa tgactgggcg    480
taaagggcgc gtaggcggtt gacacagtca aatgtaaaat tcccgggttt aacctggggg    540
ctgcttttga tacgtggcaa ctaaagtgtg aaaaagggtt gtgaaattcc cagtgtagag    600
gtgaaattcg taaatattgg aaaaaacacc ggggcaaag gcggcaacct ggctcatgac    660
tgaccctgag gcgcaaaagc gtggggagca aacaggatta aatacctgg tagtccacgc    720
tgtaaacaat gtgtgctgaa tgttgggtga ctttgtcatt cagtgtcgta tttaacgcga    780
taagcacacc gcctggggag tacggccgca aggttaaaac tcaaagaaat tgacgggggc    840
ccgcacaagc gggggagcat gtggtttatt tcaaagcaac gcgcaaaacc ttaccagggc    900
ttgacattgg gaaggccgtg tccagaaatg ggcattttct cgcaaaaaaa cctcaaccaa    960
caggtgcctg catggtttgt ctccctctcc ggtccgggaa                          1000
```